US012286668B2

(12) United States Patent
Steinhoff

(10) Patent No.: US 12,286,668 B2
(45) Date of Patent: Apr. 29, 2025

(54) SH2B ADAPTER PROTEIN 3 FOR THE PREDICTION OF BONE MARROW RESPONSE AND IMMUNE RESPONSE

(71) Applicant: UNIVERSITÄT ROSTOCK, Rostock (DE)

(72) Inventor: Gustav Steinhoff, Rethwisch (DE)

(73) Assignee: UNIVERSITÄT ROSTOCK, Rostock (DE)

(*) Notice: Subject to any disclaimer, the term of this patent is extended or adjusted under 35 U.S.C. 154(b) by 74 days.

(21) Appl. No.: 16/603,981

(22) PCT Filed: Apr. 10, 2018

(86) PCT No.: PCT/EP2018/059194
§ 371 (c)(1),
(2) Date: Oct. 9, 2019

(87) PCT Pub. No.: WO2018/189198
PCT Pub. Date: Oct. 18, 2018

(65) Prior Publication Data
US 2020/0115743 A1   Apr. 16, 2020

(30) Foreign Application Priority Data

Apr. 10, 2017 (DE) .................. 10 2017 107 661.1

(51) Int. Cl.
*C12Q 1/68* (2018.01)
*C12Q 1/6851* (2018.01)
*C12Q 1/686* (2018.01)
*C12Q 1/6883* (2018.01)
*G06F 17/18* (2006.01)

(52) U.S. Cl.
CPC ............ *C12Q 1/6851* (2013.01); *C12Q 1/686* (2013.01); *C12Q 1/6883* (2013.01); *G06F 17/18* (2013.01); *C12Q 2600/112* (2013.01); *C12Q 2600/118* (2013.01); *C12Q 2600/158* (2013.01)

(58) Field of Classification Search
CPC ........ C12Q 2600/158; C12Q 2600/112; C12Q 2660/118
See application file for complete search history.

(56) References Cited

U.S. PATENT DOCUMENTS

| | | | |
|---|---|---|---|
| 8,367,333 | B2 | 2/2013 | Gudbjartsson et al. |
| 8,945,846 | B2 | 2/2015 | Gotlib et al. |
| 10,053,734 | B2 | 8/2018 | Behrens et al. |
| 2003/0224383 | A1 | 12/2003 | West et al. |
| 2010/0160802 | A1 | 6/2010 | Gudbjartsson et al. |
| 2010/0233733 | A1* | 9/2010 | Fantl .................. G01N 33/5011 435/7.23 |
| 2012/0046233 | A1 | 2/2012 | Gotlib et al. |
| 2013/0034544 | A1 | 2/2013 | Behrens et al. |
| 2013/0253847 | A1 | 9/2013 | Gudbjartsson et al. |
| 2014/0328811 | A1 | 11/2014 | Wong et al. |
| 2016/0273044 | A1 | 9/2016 | Behrens et al. |
| 2016/0319351 | A1 | 11/2016 | Gudbjartsson et al. |
| 2017/0355958 | A1 | 12/2017 | Sankaran |
| 2019/0211398 | A1 | 7/2019 | Behrens et al. |
| 2021/0371929 | A1* | 12/2021 | Steinhoff ............. C12Q 1/6883 |

FOREIGN PATENT DOCUMENTS

| | | |
|---|---|---|
| CN | 102803509 A | 11/2012 |
| CN | 104107429 A | 10/2014 |
| CN | 104141012 A | 11/2014 |
| JP | 2007-89537 A | 4/2007 |
| JP | 2013-516988 A | 5/2013 |
| JP | 2014-526887 A | 10/2014 |
| WO | 2003/091391 A2 | 11/2003 |
| WO | 2010/067381 A1 | 6/2010 |
| WO | 2016/085934 A1 | 6/2016 |
| WO | 2016/168612 A1 | 10/2016 |

OTHER PUBLICATIONS

Gery, S., Gueller, S., Nowak, V., Sohn, J., Hofmann, W.K. and Koeffler, H.P., 2009. Expression of the adaptor protein Lnk in leukemia cells. Experimental hematology, 37(5), pp. 585-592. (Year: 2009).*

Takaki et al., 2003. Impaired lymphopoiesis and altered B cell subpopulations in mice overexpressing Lnk adaptor protein. The Journal of Immunology, 170(2), pp. 703-710. (Year: 2003).*

Afjeh, S.S.A., Ghaderian, S.M.H., Mirfakhraie, R., Piryaei, M. and Kohan, H.Z., 2014. Association study of rs3184504 C>T polymorphism in patients with coronary artery disease. International journal of molecular and cellular medicine, 3(3), p. 157-165. (Year: 2014).*

Wang, W., Tang, Y., Wang, Y., Tascau, L., Balcerek, J., Tong, W., Levine, R.L., Welch, C., Tall, A.R. and Wang, N., 2016. LNK/SH2B3 loss of function promotes atherosclerosis and thrombosis. Circulation research, 119(6), pp. e91-e103. (Year: 2016).*

Chow et al., 2017. Role of biomarkers for the prevention, assessment, and management of heart failure: a scientific statement from the American Heart Association. Circulation, 135(22), pp. e1054-e1091. (Year: 2017).*

Klein et al., Intramyocardial implantation of CD133+ stem cells improved cardiac function without bypass surgery, The heart surgery forum 10 (1) (2007) E66-69. (Year: 2007).*

Stamm et al., Intramyocardial delivery of CD133+ bone marrow cells and coronary artery bypass grafting for chronic ischemic heart disease: safety and efficacy studies, The Journal of thoracic and cardiovascular surgery 133 (3) (2007) 717-725. (Year: 2007).*

Dale, B.L. and Madhur, M.S., 2016. Linking inflammation and hypertension via LNK/SH2B3. Current opinion in nephrology and hypertension, 25(2), p. 87. (Year: 2016).*

(Continued)

*Primary Examiner* — Stephanie K Mummert
*Assistant Examiner* — Olayinka A Oyeyemi
(74) *Attorney, Agent, or Firm* — Studebaker Brackett PLLC

(57) ABSTRACT

The present invention relates to SH2B adapter protein 3 (SH2B3) for use as a diagnostic marker. Further, the present invention relates to a method for the determination of SH2B3 gene expression.

7 Claims, 1 Drawing Sheet

(56) References Cited

OTHER PUBLICATIONS

Ahlenius et al., 2012. Adaptor protein LNK is a negative regulator of brain neural stem cell proliferation after stroke. Journal of Neuroscience, 32(15), pp. 5151-5164. (Year: 2012).*
Flister et al., 2015. SH2B3 is a genetic determinant of cardiac inflammation and fibrosis. Circulation: Cardiovascular Genetics, 8(2), pp. 294-304. (Year: 2015).*
McPherson, R. and Tybjaerg-Hansen, A., 2016. Genetics of coronary artery disease. Circulation research, 118(4), pp. 564-578. (Year: 2016).*
Stamm et al., 2003. Autologous bone-marrow stem-cell transplantation for myocardial regeneration. The Lancet, 361(9351), pp. 45-46. (Year: 2003).*
Lee et al., 2016. Specific disruption of Lnk in murine endothelial progenitor cells promotes dermal wound healing via enhanced vasculogenesis, activation of myofibroblasts, and suppression of inflammatory cell recruitment. Stem cell research & therapy, 7(1), pp. 1-12. (Year: 2016).*
Steinhoff et al., Epub Jul. 29, 2017. Cardiac function improvement and bone marrow response-: Outcome analysis of the randomized perfect phase iii clinical trial of intramyocardial cd133+ application after myocardial infarction. EBioMedicine, 22, pp. 208-224. (Year: 2017).*
International Search Report issued in PCT/EP2018/059194; mailed May 29, 2018.
Devalliere, Julie; Charreau Beatrice, "The adaptor Lnk (SHZB3): An emerging regulator in-vascular cells and a link between immune and inflammatory signaling", Biochemical Pharmacology, Elsevier, US, vol. 82, No. 10, Jun. 16, 2011 (Jun. 16, 2011), pp. 1391-1402.
Spolverini, Ambra, et al. "Infrequent occurrence of mutations in the PH domain of LNK in pa-tients with JAK2 mutation-negative 'idiopathic' erythrocytosis." Haematologica, 2013, vol. 98, No. 9, pp. e101-e102.
Ge, Zheng, et al. "Co-existence of IL7R high and SH2B3 low expression distinguishes a novel high-risk acute ymphoblastic leukemia with Ikaros dysfunction." Oncotarget, 2016, vol. 7., No. 29, p. 46014.
Dale Bethany L et al: "Linking inflammation and hypertension via LNK/SH2B3", Current Opinion in Nephrology & Hypertension, Lippincott Williams & Wilkins, Ltd, GB, vol. 25, No. 2, Feb. 29, 2016 (Feb. 29, 2016), pp. 87-93.
Ding L-W et al: "LNK (SH2B3): paradoxical effects in ovarian cancer", Oncogene, vol. 34, No. 11, Mar. 2015 (Mar. 2015), pp. 1463-1474.
Stamm et al: "Intramyocardial delivery of CD133A+ bone marrow cells and coronary artery bypass grafting for chronic ischemic heart disease: Safety and efficacy studies", Journal of Thoracic and Cardiovascular Surg, Mosby-Yearbook, Inc., St. Louis, MO, US, vol. 133, No. 3, Feb. 21, 2007 (Feb. 21, 2007), pp. 717-725.e5.
Steinhoff Gustav et al: "Stem cells and heart disease—Brake or accelerator?", Advanced Drug Delivery Reviews, vol. 120, Oct. 18, 2017 (Oct. 18, 2017), pp. 2-24.
Steinhoff Gustav et al: "Cardiac Function Improvement and Bone Marrow Response -: Outcome Analysis of the Randomized Perfect Phase III Clinical Trial of Intramyocardial CDI33<+>Application After Myocardial Infarction.", Ebiomedicine Aug. 2017, vol. 22, Aug. 2017 (Aug. 2017), pp. 208-224.
An Office Action mailed by the Japanese Patent Office on Jan. 25, 2022, which corresponds to Japanese Patent Application No. 2019-556232 and is related to U.S. Appl. No. 16/603,981; with English language translation.
Huan, Tianxiao et al.; "A Meta-analysis of Gene Expression Signatures of Blood Pressure and Hypertension"; PLoS Genetics, vol. 11 No. 3; e1005035; Mar. 18, 2015; pp. 1-29; doi: 10.1371/journal.pgen.1005035.
Kwon, Sang-Mo et al.; "Pivotal Role of Lnk Adaptor Protein in Endothelial Progenitor Cell Biology for Vascular Regeneration"; Circulation Research, vol. 104 No. 8; Mar. 26, 2009; pp. 969-977; doi: 10.1161/CIRCRESAHA.108.192856.
An Office Action mailed by the State Intellectual Property Office of the People's Republic of China on Nov. 2, 2022, which corresponds to Chinese Patent Application No. 201880024292.9 and is related to U.S. Appl. No. 16/603,981; with English language translation.

* cited by examiner

SH2B3 gene expression analysis in peripheral blood of responder and non-responder
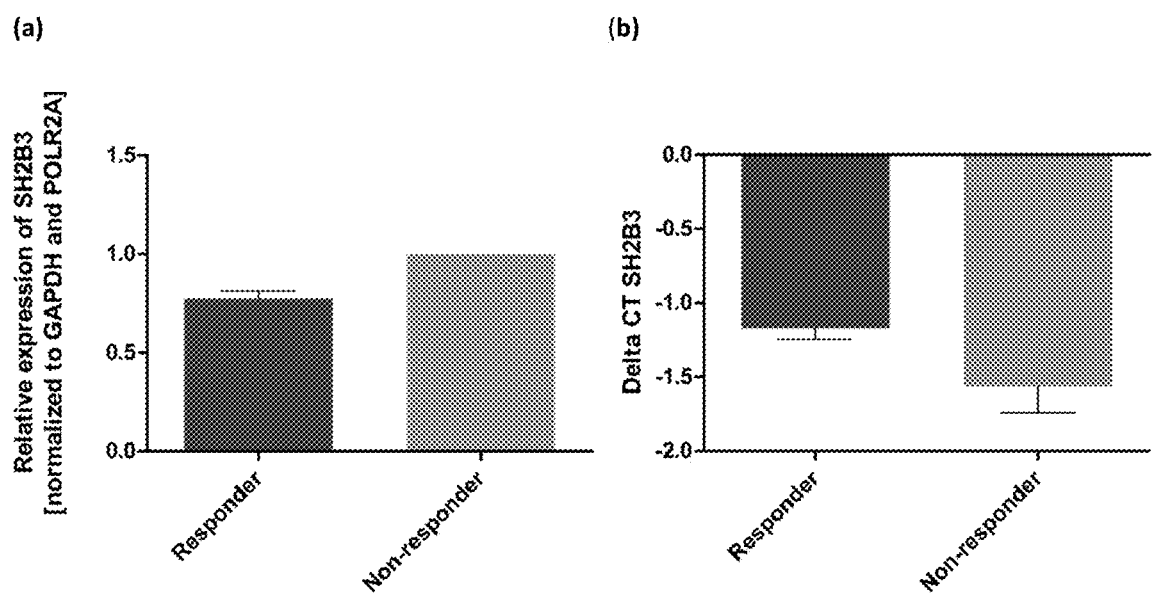

SH2B ADAPTER PROTEIN 3 FOR THE PREDICTION OF BONE MARROW RESPONSE AND IMMUNE RESPONSE

The present invention relates to SH2B adapter protein 3 (SH2B3) for use as a diagnostic marker. Further, the present invention relates to a method for the determination of SH2B3 gene expression.

SH2B3, also known as lymphocyte adapter protein (LNK), is a protein that, in humans, is encoded by the SH2B3 gene on chromosome 12. It is ubiquitously expressed in many tissues and cell types ("*BioGPS-your Gene Portal System*". biogps.org. Retrieved 2016-10-11). SH2B3 functions as a regulator in signaling pathways relating to hematopoiesis, inflammation and cell migration (Devallière J, Charreau B (November 2011). Biochemical Pharmacology. 82 (10): 1391-402. doi:10.1016/j.bcp.2011.06.023. PMID 21723852). As a result, it is involved in blood diseases, autoimmune disorders and vascular disease (Auburger G, Gispert S, Lahut S, Omür O, Damrath E, Heck M, Başak N (June 2014). Wourld Journal of Diabetes. 5 (3): 316-27. doi:10.4239/wjd.v5.i3.316. PMC 4058736. PMID 24936253). The SH2B3 gene also contains one of 27 single nucleotide polymorphisms (SNPs) associated with increased risk of coronary artery disease, type 1 diabetes mellitus and rheumatoid arthritis (Mega J L, Stitziel N O, Smith J G, Chasman D I, Caulfield M J, Devlin J J, Nordio F, Hyde C L, Cannon C P, Sacks F M, Poulter N R, Sever P S, Ridker P M, Braunwald E, Melander O, Kathiresan S, Sabatine M S (June 2015). Lancet. 385 (9984): 2264-71. doi:10.1016/S0140-6736(14)61730-X PMC 4608367. PMID 25748612).

Regenerative therapies using stem cells for the repair of heart tissue have been at the forefront of preclinical and clinical development in the last 16 years. Among the different approaches the direct application of bone marrow stem cells in heart tissue still has the most dedicated clinical developmental attention since the first-in-man application in 2001 and the initial promising clinical trials (Stamm C, Westphal B, Kleine H D, et al. Lancet. 2003; 361(9351): 45-46; Tse H F, Kwong Y L, Chan J K, Lo G, Ho C L, Lau C P. Lancet 2003; 361(9351):47-9; Stamm C, Kleine H D, Choi Y H, et al. J Thorac Cardiovasc Surg 2007; 133(3): 717-25). So far, however, efficacy could not be demonstrated in any of the subsequent placebo controlled Phase II trials (Timothy D. Henry, Lem Moyé, Jay H. Traverse. Circulation Research 2016; 119:404-406; Nasseri B A, Ebell W, Dandel M, et al. Eur Heart J 2014; 35(19):1263-74; Bartunek J, Terzic A, Davison B A, et al. Eur Heart J 2016 Dec. 23. pii: ehw543. doi: 10.1093/eurheartj/ehw543).

This has raised the question of induction of regenerative mechanisms independent of stem cell application and potential suppressive factors of vascular repair associated with CD34$^+$ EPC (Werner N, Kosiol S, Schiegl T, et al. N Engl J Med. 2005; 353(10):999-1007). In respect of the recent published assumption it should be noted that the pivotal role of CD133/CD34$^+$ peripheral circulating EPC could be related to lack of cardiac regeneration (Taylor D A, Perin E C, Willerson J T, et al. Cell Transplant 2016; 25(9):1675-1687; Bhatnagar A, Bolli R, Johnstone B H, et al. Am Heart J 2016; 179:142-50; Contreras A, Orozco A F, Resende M, et al. Basic Res Cardiol 2017;112(1):3).

Thus, the question of the mechanism of cardiac regeneration and role of bone marrow stem cell regulated angiogenesis still remains unsolved.

The inventors have now identified SH2B3 gene induction to be related to the suppression or induction of response of several biochemical processes.

The present invention is thus directed to SH2B adaptor protein 3 and its gene expression for use as a diagnostic marker.

According to the invention, expression of SH2B3 gene in different cell systems and tissues as well as the response related thereto advantageously allow for the identification of underlying mechanism of the different diseases (as depicted below). In addition, gene expression of SH2B3 in the different cell systems and response mechanism are used for diagnosis and predictive therapy of subjects to beneficit from efficient medical treatment.

Preferably, SH2B3 is used for the in vitro/ex vivo diagnosis, in particular for medical use.

The present invention also relates to a method for investigation of SH2B3 gene expression, the method comprising:
i. blood sampling of a subject
ii. determination of SH2B3 gene expression, preferably by RT-PCR and/or qPCR,
iii. classification into responder or non-responder.

According to the invention, predictive diagnosis for subjects, e.g. patients, as to their response behavior, i.e. whether they are classified to respond to a certain treatment ("responder") or not ("non-responder"), is allowed. Advantageously, a subject which is classified as non-responder would therefore not be selected to undergo a therapy he would not benefit from, thereby reducing adverse drug reaction usually suffered by treatment with drug products. In addition, therapy of the subject can be reduced to focus on effective treatment, thereby also reducing cost-effective therapies.

Preferably, the method of the present invention is an in vitro/ex vivo method. Moreover, it may comprise steps in addition to those explicitly mentioned above. For example, further steps may relate to sample pre-treatments or further evaluations or uses of the results obtained by the method. The method may be carried out manually or assisted by automation. Preferably, step (i) may in total or in part be assisted by automation, e.g. by a suitable robotic and sensory equipment. Steps (ii) and/or (iii) may be assisted by data processing units which carry out the respective comparisons and/or predictions as detailed above.

Preferably, determination of SH2B3 gene expression is used in the diagnosis for the prediction of bone marrow response and immune response, wherein the term "diagnosis" preferably refers to an in vitro/ex vivo diagnosis. In particular, determination of SH2B3 gene expression is used in the diagnosis for predictive treatment of subjects suffering from a disease in which predictive therapy is of benefit.

The term "subject" as used herein refers to an animal, preferably, a mammal and, most preferably, a human. In accordance with the invention, a sample of such a subject may be derived from blood, in particular peripheral blood, and/or a serum and/or a plasma sample and/or a tissue biopsy sample and/or a sample of circulating (stem) cells such as endothelial progenitor cells (EPC).

Determining the amount of SH2B3 or its gene expression referred to in this specification relates to measuring the amount or concentration, preferably, semi-quantitatively or quantitatively. Measuring can be done directly or indirectly. Direct measuring relates to measuring the amount or concentration of SH2B3 based on a signal which is obtained from the SH2B3 itself and the intensity of which directly correlates with the number of molecules of the SH2B3 present in the sample. Such a signal—sometimes referred to herein as intensity signal—may be obtained, e.g. by measuring an intensity value of a specific physical or chemical property of SH2B3. Indirect measuring includes measuring of a signal obtained from a secondary component (i.e. a component not being SH2B3 itself) or a biological read out system, e.g. measurable cellular responses, ligands, labels, or enzymatic reaction products.

In accordance with the present invention, determining the amount of SH2B3 can be achieved by all known means for determining the amount of a peptide, a protein, a small molecule, nucleic acids such as DNAs or RNAs or a cell or subpopulations thereof, in a sample. Said means comprise immunoassays and methods which may utilize labelled molecules in various sandwich, competition, or other assay formats. Such assays are, preferably, based on detection agents such as antibodies which specifically recognize SH2B3 or its gene expression to be determined. The detection agents shall be either directly or indirectly capable of generating a signal indicating the presence or absence of SH2B3. Moreover, the signal strength can, preferably, be correlated directly or indirectly (e.g. reverse-proportional) to the amount of SH2B3 present in a sample. Further suitable methods comprise measuring a physical or chemical property specific for SH2B3 such as its precise molecular mass or NMR spectrum. Said methods comprise, preferably, biosensors, optical devices coupled to immunoassays, FACS analysis, biochips, analytical devices such as mass-spectrometers, NMR-analysers, or chromatography devices. Further, methods include micro-plate ELISA-based methods, fully automated or robotic immunoassays, enzymatic Cobalt binding assays, and latex agglutination assays.

Preferably, determining the amount of a SH2B3 or its gene expression, respectively, comprises the steps of (a) contacting a cell, e.g. a blood cell, capable of eliciting a cellular response the intensity of which is indicative of the amount of SH2B3 for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of SH2B3.

Also preferably, determining the amount of SH2B3 comprises the step of measuring a specific intensity signal obtainable from SH2B3 in the sample. As described above, such a signal may be the signal intensity observed at an m/z variable specific for SH2B3 observed in mass spectra or an NMR spectrum specific for SH2B3.

The term "amount" as used herein encompasses the absolute amount of SH2B3, the relative amount or concentration of SH2B3 as well as any value or parameter which correlates thereto or can be derived therefrom. Such values or parameters comprise intensity signal values from all specific physical or chemical properties obtained from said peptides by direct measurements, e.g. intensity values in mass spectra or NMR spectra. Moreover, encompassed are all values or parameters which are obtained by indirect measurements specified elsewhere in this description, e.g. response levels determined from biological read out systems in response to the peptides or intensity signals obtained from specifically bound ligands. It is to be understood that values correlating to the aforementioned amounts or parameters can also be obtained by all standard mathematical operations and can be used without dimensions, e.g. in scoring systems as described elsewhere herein.

The classification referred to in the method of the present invention may be carried out manually or computer assisted. For a computer assisted classification, the value of the determined amount may be compared to values corresponding to suitable references which are stored in a database by a computer program. The computer program may further evaluate the result of the comparison, i.e. automatically provide the desired assessment in a suitable output format. Preferably, such an assessment is performed by machine learning (ML). Based on the comparison of the determined amounts and the reference, it is possible to predict a response, e.g. a functional improvement of the heart after cardiac stem cell therapy. In particular, it shall be possible to classify and to predict whether there is a high probability (i.e. the subject will be a responder), a low probability (i.e. the subject will be a non-responder) or the subject is ambivalent. Therefore, the reference amount is to be chosen so that either a difference or a similarity in the compared amounts allows identifying those test subjects.

The term "reference" as used herein refers to a value, threshold or interval based on amount of SH2B3 which allows for allocation of a subject into either the group of subjects which can be expected to benefit from therapy or which can be expected not to benefit therapy or those which are ambivalent.

The term "sample" refers to a sample of a body fluid, and preferably, to a sample of (whole) blood, plasma or serum. The term, however, also encompasses all samples which are derived from the aforementioned whole blood, plasma or serum by, e.g. pre-treatment steps such as fractions of blood, plasma or serum obtained by, e.g. partial purification.

Further preferred embodiments of the invention are derived from the dependent claims together with the following description, whereby the patent claims of a certain category may be formed by dependent claims of a different category, and features of the different examples may be combined to new examples. It is to be understood that the definitions and explanations of the terms made above and below apply accordingly for all embodiments described in this specification and the accompanying claims. In the following, particular embodiments of the method of the present invention are specified further.

According to a prefered embodiment SH2B3 is used in the diagnosis for the prediction of bone marrow response and immune response. The term "diagnosis" preferably refers to an in vitro/ex vivo diagnosis.

The term "predicting" as used herein means assessing the probability according to which a subject will benefit from e.g. bone marrow response and/or immune response etc. The prediction made according to the invention allows for assessing whether the probability is high and, thus, it is expected that a functional improvement, e.g. of the cardiac system in a subject occurs, or whether the probability is such that the therapy success is ambivalent or whether the probability is low and, thus, it is expected that a functional improvement in a subject will not occur.

As will be understood by those skilled in the art, such an assessment is usually not intended to be correct for 100% of the subjects to be diagnosed. The term, however, requires that the assessment is correct for a statistically significant portion of the subjects (e.g. a cohort in a cohort study). Whether a portion is statistically significant can be determined without further ado by the person skilled in the art using various well known statistic evaluation tools, e.g., by determination of confidence intervals, p-value determination, Student's t-test, Mann-Whitney test etc. Details are found, e.g., in Dowdy and Wearden, Statistics for Research, John Wiley & Sons, New York 1983. Advantageously, the method of the present application may encompass the classification to be conducted via analysis of covariance (ANCOVA) and/or two-sample t-test.

Preferably, the expression of the SH2B3 gene is quantitatively detected on the level of RNA, more preferably on the level of mRNA, thereby allowing for a fast and accurate measurement of SH2B3 gene expression Gene expression of SH2B3 for use as a diagnostic marker may not only encompass natural variants of human or non-human SH2B3 whole sequence but also parts of its sequence as well as modifications thereof, as depicted, e.g. by www.uniprot.org/uniprot/Q9UQQ2 or O09039 or by www.genecards.org/cgi-bin/carddisp.pl?gene=SH2B3. In particular, also a gene expression pattern of SH2B3 in body liquid(s) and/or tissues and/or cells, as, e.g., of whole blood, CD14 monocytes, CD33 myeloids, BDCA4 dendritic cells, CD56 NK-cells, CD4 T-cells, CD8 T-cells etc. may be determined. However, expression of the SH2B3 gene or gene pattern may, alternatively or additionally, also be determined by indirect methods on the protein level, such as, e.g., by detection via antibodie(s) binding to SH2B3.

According to a preferred embodiment, the present invention is directed to SH2B3 in the diagnosis for the prediction of proliferation and inflammation response of bone marrow stem (progenitor) cells or non-bone marrow stem (progenitor) cells and/or blood cells and/or immune cells and/or vascular cells and/or tissue cells.

A further preferred embodiment is directed to SH2B3 for use as a diagnostic marker for the prediction of the expression of endothelial activation or suppression of Integrin Receptors or Erythropoeitin (EPO) Receptor or stem cell factor (CD105) or VEGF-REC (CD309) or stem cell proliferation factor (CD117) or Notch receptor.

The term "Integrin Receptor" as used herein refers to transmembrane receptors that facilitate cell-extracellular matrix (ECM) adhesion. Upon ligand binding, integrins activate signal transduction pathways that mediate cellular signals such as regulation of the cell cycle, organization of the intracellular cytoskeleton, and movement of new receptors to the cell membrane.

The term "Erythropoeitin (EPO)" as used herein refers to a soluble polypeptide being a cytokine. It is produced by kidney cells, typically, under hypoxic conditions.

Preferably, EPO refers to human IL-6 as described, e.g. in Yanagawa 1984, J. Biol. Chem. 259(5): 2707-2710. More preferably, human IL-6 has an amino acid sequence as shown in Genbank accession number p01588.1, GI: 119526. The term also encompasses variants of the aforementioned human EPO polypeptides. Such variants have at least the same essential biological and immunological properties as the aforementioned EPO polypeptide. In particular, they share the same essential biological and immunological properties if they are detectable by the same specific assays referred to in this specification, e.g., by ELISA assays using polyclonal or monoclonal antibodies specifically recognizing the said EPO polypeptides. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific IL-6. Variants may be allelic variants, splice variants or any other species specific homologs, paralogs, or orthologs. Moreover, the variants referred to herein include fragments of the specific EPO or the aforementioned types of variants as long as these fragments have the essential immunological and biological properties as referred to above. Such fragments may be, e.g., degradation products of EPO. Variants are deemed to share the same essential biological and immunological properties if they are detectable by the same specific assays referred to in this specification, e.g., by ELISA assays using polyclonal or monoclonal antibodies specifically recognizing the said EPO polypeptides. A preferred assay is described in the accompanying Examples. Further included are variants which differ due to posttranslational modifications such as phosphorylation or myristylation.

The term "VEGF-REC (CD309)" refers to the kinase insert domain receptor (KDR, a type III receptor tyrosine kinase), also known as vascular endothelial growth factor receptor 2 (VEGFR-2). KDR is the human gene encoding it. KDR has also been designated as CD309 (cluster of differentiation 309). KDR is also known as Flk1 (Fetal Liver Kinase 1).

The term "stem cell" as used herein refers to biological cells that can differentiate into other types of stem cells and can divide to produce more of the same type of stem cells. They are found in multicellular organisms. Stem cell factor (CD105) is also know as endoglin and is a major cell membrane glycoprotein expressed in stem cells.

The term "stem cell factor receptor (SCFR)" is also known as proto-oncogene c-Kit or tyrosine-protein kinase Kit or CD117 and is a receptor tyrosine kinase protein that in humans is encoded by the KIT gene. Multiple transcript variants encoding different isoforms have been found for this gene.

The term "Notch receptor" refers to Notch proteins, e.g., referred to as NOTCH1, NOTCH2, NOTCH3 and NOTCH 4. The Notch receptor is a single-pass transmembrane receptor protein. It is a hetero-oligomer composed of a large extracellular portion, which associates in a calcium-dependent, non-covalent interaction with a smaller piece of the notch protein composed of a short extracellular region, a single transmembrane-pass, and a small intracellular region.

A next preferred embodiment relates to SH2B3 for use as a diagnostic marker for the prediction of expression of bone marrow stem (progenitor) cell (CD133+ of MSC) activation or suppression of Integrin Receptors or Erythropoeitin Receptor or stem cell factor (CD105) or VEGF-REC (CD309) or CXCR4 (CD184) or stem cell proliferation factor (CD117) or Notch receptor.

The term "expression of bone marrow stell cell activation" refers to the expression of CD133 (=CD133+) on mesenchymal stem cells (MSC) of bone marrow. "CD133" is an antigen, also known as prominin-1, that in humans is encoded by the PROM1 gene. It is a member of pentaspan transmembrane glycoproteins (5-transmembrane, 5-TM), which specifically localize to cellular protrusions.

The term "CXCR-4" refers to C-X-C chemokine receptor type 4, also known as fusin or CD184 (cluster of differentiation 184), and is a protein that in humans is encoded by the CXCR4 gene.

An even further preferred embodiment encompasses SH2B3 for use as a diagnostic marker for the prediction of release of EPO and VEGF into peripheral blood.

The term "vascular endothelial growth factor (VEGF)" as used herein refers to soluble polypeptide growth factor which stimulates angiogenesis, vasculogenesis and vascular permeability. It is produced by various cell types. There are five different VEGF polypeptides, VEGF-A, placenta growth factor (PGF), VEGF-B, VEGF-C, and VEGF-D. As used herein, preferably, VEGF-A is envisaged. There are various isoforms resulting from alternative splicing known for VEGF-A. The most prominent ones are $VEGF_{121}$, $VEGF_{121}b$, $VEGF_{145}$, $VEGF_{165}$, $VEGF_{165}b$, $VEGF_{189}$, and $VEGF_{206}$.

Preferably, VEGF refers to human VEGF-A as described in Tischer 1991, J. Biol. Chem. 266 (18): 11947-11954 (disclosed is the longest isoform for VEGF-A). For amino acid sequences, see, e.g., also Genbank accession numbers NP_001020537.2, GI: 76781480 (Genbank is available from the NCBI, USA under www.ncbi.nlm.nih.gov/entrez). The term also encompasses variants of the aforementioned human VEGF polypeptides. Such variants have at least the same essential biological and immunological properties as the aforementioned VEGF polypeptide. In particular, they share the same essential biological and immunological properties if they are detectable by the same specific assays referred to in this specification, e.g. by ELISA assays using polyclonal or monoclonal antibodies specifically recognizing the said VEGF polypeptides. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 99% identical with the amino sequence of the specific VEGF polypeptide, preferably over the entire length of the human VEGF, respectively. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm disclosed by Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, FAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Variants referred to above may be allelic variants or any other species specific homologs, paralogs, or orthologs. Moreover, the variants referred to herein include fragments or subunits of the specific VEGF polypeptides or the aforementioned types of variants as long as these fragments have the essential immunological and biological properties as referred to above. Such fragments may be, e.g., degradation products of the VEGF polypeptides. Variants are deemed to share the same essential biological and immunological properties if they are detectable by the same specific assays referred to in this specification, e.g., by ELISA assays using polyclonal or monoclonal antibodies specifically recognizing the said VEGF polypeptides.

According to another preferred embodiment SH2B3 is used as a diagnostic marker for the prediction of release of inflammatory cytokines (e.g. TNF alpha, IP-10, Interleukins) into peripheral blood.

Another preferred embodiment is directed to SH2B3 for use as a diagnostic marker for the prediction of (stem-) cell response to release of EPO and VEGF into peripheral blood.

A next embodiment is related to SH2B3 for use as a diagnostic marker for the prediction of (stem-) cell response to release to inflammatory cytokines or growth factors into peripheral blood.

An even further embodiment relates to SH2B3 for use as a diagnostic marker for the prediction of (stem-) cell response to peripheral blood levels of drug, nutrients, (nano-)particles, micro-RNA, proteins, infusion solutions, and/or toxic reagents into peripheral blood.

According to a next embodiment SH2B3 is used as a diagnostic marker for the prediction of angiogenesis stimulation, in particular by bone marrow stem cell (CD133+) proliferation and release of EPC (CD133+, CD117+, CD34+) binding to peripheral VEGF-REC.

Still another preferred embodiment relates to SH2B3 for use as a diagnostic marker for the prediction of megakaryocyte stimulation or suppression, in particular by bone marrow stem cell (CD133+) proliferation and release of thrombocytes.

According to a next embodiment, SH2B3 is used as a diagnostic marker for the prediction of hematopoiesis proliferation stimulation or suppression or proliferation, in particular by bone marrow stem cell (CD133+) proliferation and release of erythrocytes, myeloid cells and lymphocytes.

A further embodiment is directed to SH2B3 for use as a diagnostic marker for the prediction of endothelial or vascular progenitor cell or MSC proliferation stimulation or suppression of proliferation.

A next embodiment addresses SH2B3 for use as a diagnostic marker for the prediction of expression of endothelial activation of stem cell factor (SCF) or Integrin receptor or cell adhesion receptor.

Another embodiment addresses SH2B3 for use as a diagnostic marker for the prediction of expression of endothelial activation of Erythropoeitin Receptor or VEGF-REC.

An even next embodiment is directed to SH2B3 for use as a diagnostic marker for the prediction of expression of leucocyte or lymphocyte Integrin receptor expression.

A further embodiment relates to SH2B3 for use as a diagnostic marker for the prediction of repair of peripheral tissue and oxygenation.

Another embodiment is directed to SH2B3 for use as a diagnostic marker for the prediction of bone marrow response or bone marrow failure or bone marrow stem cell proliferation response or bone marrow release of blood cells.

A further embodiment encompasses SH2B3 for use as a diagnostic marker for the prediction of inflammatory response of blood cells or immune cells or hematopoietic (CD133+) stem cells, bone marrow cells or tissue cells or endothelial cells or non-hematopoeitic stem cells.

The term "hematopoietic stem cell (HSC)" refers to the stem cells that give rise to other blood cells. This process is called haematopoiesis. The process occurs in the red bone marrow, in the core of most bones.

Just another embodiment relates to SH2B3 for use as a diagnostic marker for the prediction of bone marrow stem cell proliferation and release of EPC CD133+.

An even further embodiment is directed to SH2B3 for use as a diagnostic marker for use in the treatment of peripheral ischemia and inflammation.

According to another embodiment SH2B3 is used as a diagnostic marker in the therapy of vascular repair, cardiac regeneration and atherosclerosis.

Still another embodiment relates to SH2B3 for use in the treatment of subjects with heart failure after myocardial infarction, ischemic cardiomyopathy and coronary artery disease.

The term "heart failure" as used herein refers to any functional impairment of the heart including left-sided failures, right-sided failures or biventricular failures. Typically, the term heart failure as referred to herein is left-sided failure that results in reduced ejection fractions, e.g. a significantly reduced LVEF (Left Ventricular Ejection Fraction). Further symptoms of heart failure are well known to the clinician. Heart failure as referred to herein encompasses acute and chronic forms of heart failure and any stage of severity, e.g. for left-sided failures all stages according to the New York Heart Association (NYHA) classification system, NYHA I to IV.

A next embodiment is directed to SH2B3 for use as a diagnostic marker for the therapy of LVEF recovery.

The term "recovery" as used herein refers to an increase in the LVEF of the heart observed when comparing said LVEF before and after treatment of the subject. Preferably, a significant increase is an increase of 5% or more of LVEF observed after treatment. Further parameters which may be considered in addition for finding a functional improvement are a more than 10% decrease in perfusion defect size, a more than 10% decrease in left ventricle end systolic volume (LVESV) as quantified by MIBI SPECT and a more than 10% increase in peak systolic velocity measured by transthoracic echocardiogram.

An even next embodiment encompasses SH2B3 for use as a diagnostic marker in cardiac, vascular or non-cardiovascular tissue regeneration, selection of responding patients and monitoring of angiogenesis response.

The term "cardiac, vascular or cardiovascular tissue regeneration" as used herein includes the regeneration and/or treatment and/or improvement of diseases related to the cardiac, vascular or cardiovascular system.

A further preferred embodiment relates to SH2B3 for use as a diagnostic marker for the treatment of subjects with ischemic disease, stroke, peripheral ischemia, (poly-) trauma, resuscitation, shock, septic inflammatory response syndrome (SIRS), and/or sepsis.

Advantageous, SH2B3 for use as a diagnostic marker is used for the treatment of subjects with infectious disease, viral disease, irradiation exposure, chemotherapy, drug side effects and/or cancer.

Though SH2B3 for use as a diagnostic marker according to the invention is highly advantageous for use in human subjects, it is not restricted to humans but might also be used for non-human subjects.

A preferred method is directed to the prediction whether a subject is a responder or non-responder and includes the following steps:
(i) blood sampling of a subject
(ii) determination of SH2B3 gene expression, preferably by RT-PCR and/or qPCR,
(iii) comparing the determined amounts to a baseline value and/or a reference,
(iv) classification into responder or non-responder.

The preferred method is advantageously used for in vitro/ex vivo diagnosis and is used for medical use.

A preferred method comprises tissue sampling of a subject. Tissue sampling might be performed alternatively to blood sampling.

According to a prefered method blood and/or tissue samples are obtained by pre-treatment steps, in particular fractions of blood, plasma or serum obtained by, e.g. partial purification.

Another preferred method encompasses the classification of bone marrow stem cell responder versus non-responder.

A further preferred method encompasses the classification of inflammation responder versus non-responder.

According to a next preferred embodiment, a preferred method addresses subjects suffering from coronary artery disease, atherosclerosis, celiac disease, type 1 diabetes mellitus, infectious disease, autoimmune disease, and/or rheumatoid arthritis.

According to a preferred embodiment, the method is used in the diagnosis for the prediction of proliferation and inflammation response of bone marrow stem (progenitor) cells or non-bone marrow stem (progenitor) cells and/or blood cells and/or immune cells and/or vascular cells and/or tissue cells.

A further preferred method is used for the prediction of the expression of endothelial activation or suppression of Integrin Receptors or Erythropoeitin (EPO) Receptor or stem cell factor (CD105) or VEGF-REC (CD309) or stem cell proliferation factor (CD117) or Notch receptor.

A next preferred method is used for the prediction of expression of bone marrow stem (progenitor) cell (CD133+ of MSC) activation or suppression of Integrin Receptors or Erythropoeitin Receptor or stem cell factor (CD105) or VEGF-REC (CD309) or CXCR4 (CD184) or stem cell proliferation factor (CD117) or Notch receptor.

An even further preferred method is used for the prediction of release of EPO and VEGF into peripheral blood.

According to another preferred method is used for the prediction of release of inflammatory cytokines (e.g. TNF alpha, IP-10, Interleukins) into peripheral blood.

Another preferred method is used for the prediction of (stem-) cell response to release of EPO and VEGF into peripheral blood.

A next method is used for the prediction of (stem-) cell response to release inflammatory cytokines or growth factors into peripheral blood.

An even further method is used for the prediction of (stem-) cell response to peripheral blood levels of drug, nutrients, (nano-)particles, micro-RNA, proteins, infusion solutions, and/or toxic reagents into peripheral blood.

According to a next preferred embodiment, the method is used for the prediction of angiogenesis stimulation, in particular by bone marrow stem cell (CD133+) proliferation and release of EPC (CD133+, CD117+, CD34+) binding to peripheral VEGF-REC.

Still another preferred method is used for the prediction of megakaryocyte stimulation or suppression, in particular by bone marrow stem cell (CD133+) proliferation and release of thrombocytes.

According to a next embodiment, the method is used for the prediction of hematopoiesis proliferation stimulation or suppression or proliferation, in particular by bone marrow stem cell (CD133+) proliferation and release of erythrocytes, myeloid cells and lymphocytes.

A further method is used for the prediction of endothelial or vascular progenitor cell or MSC proliferation stimulation or suppression of proliferation.

A next preferred method is used for the prediction of expression of endothelial activation of stem cell factor (SCF) or Integrin receptor or cell adhesion receptor.

Another method is used for the prediction of expression of endothelial activation of Erythropoeitin Receptor or VEGF-REC.

An even next method is used for the prediction of expression of leucocyte or lymphocyte Integrin receptor expression.

A further method is used for the prediction of repair of peripheral tissue and oxygenation.

Another method is used for the prediction of bone marrow response or bone marrow failure or bone marrow stem cell proliferation response or bone marrow release of blood cells.

A further method is used for the prediction of inflammatory response of blood cells or immune cells or hematopoietic (CD133+) stem cells, bone marrow cells or tissue cells or endothelial cells or non-hematopoeitic stem cells.

Just another method is used for the prediction of bone marrow stem cell proliferation and release of EPC CD133+.

An even further method is used for the treatment of peripheral ischemia and inflammation.

According to another embodiment, the method is used in the therapy of vascular repair, cardiac regeneration and atherosclerosis.

Still another method is used for the treatment of subjects with heart failure after myocardial infarction, ischemic cardiomyopathy and coronary artery disease.

A next method is used for the therapy of LVEF recovery.

An even next method is used in cardiac, vascular or non-cardiovascular tissue regeneration, selection of responding patients and monitoring of angiogenesis response.

A further preferred method is used for the treatment of subjects with ischemic disease, stroke, peripheral ischemia, (poly-)trauma, resuscitation, shock, septic inflammatory response syndrome (SIRS), and/or sepsis.

An even further method is used for the treatment of subjects with infectious disease, viral disease, irradiation exposure, chemotherapy, drug side effects and/or cancer.

Advantageously, the method of the present application may encompass the classification to be conducted via analysis of covariance (ANCOVA) and/or two-sample t test.

Further characteristics of the present invention are derived from the examples in combination with the claims and the figure. Single features may be, in a particular embodiment, realised in combination with other features and do not limit the scope of protection of the present invention. The following description of the examples according to the invention may relate to the figure, whereby FIG. 1 depicts SH2B3 gene expression analysis in peripheral blood of responder and non-responder.

EXAMPLES

Example 1

Intramyocardial CD133+ purified autologous bone marrow stem cell (BMSC) transplantation has been investigated as an adjunctive strategy to coronary artery bypass graft (CABG) revascularization to recover left ventricular heart function following deteriotation of left ventricular ejection fraction (LVEF) after acute myocardial ST-segment elevation infarction (STEMI) and coronary artery 3-vessel disease sequentially treated by acute PCI and secondary CABG revascularization. Previous safety and efficacy (phase I, IIa, IIb) trials have demonstrated enhancement of left ventricular ejection fraction (LVEF) and clinical safety of adjunctive CD133+ BMSC treatment to coronary revascularization. The randomized double-blinded placebo controlled clinical trial was designed to assess clinical safety, efficacy and biomarkers to identify CD133+ bone marrow stem cell related cardiac repair mechanism by interventional CD133+ BMSC transplantation.

A randomized double-blinded placebo controlled phase III clinical trial was conducted to assess clinical safety and efficacy of intramyocardial CD133+ bone marrow stem cell treatment combined with coronary artery bypass surgery (CABG) for induction of cardiac regeneration.

DESIGN: Multicentre, double-blinded, randomised placebo controlled trial according to GCP-ICH.

PARTICIPANTS: Eligible patients were post-infarction patients with chronic ischemia, coronary artery stenosis, and reduced LVEF (25-50%).

INTERVENTIONS: Eighty two patients were randomised to two groups receiving intramyocardial application of 5 ml placebo or a suspension of $0.5-5\times10^6$ purified autologous CD133+ bone marrow stem cells combined with CABG revascularization.

OUTCOME: Primary endpoint was delta ($\Delta$) LVEF at 6 m/0 measured in MRI

FINDINGS: Prespecified analysis: Overall efficacy population (n=58) from baseline LVEF 33.5±6.3·%. by 9.6±11.6%, p=0.001. Placebo (n=30) 8.2±2.1 (−11.2-−4.5), p<0.001. CD133+ group (n=28) 1.1±13.7 SD, CI−16.7-−6.1, p<0.001. Placebo/CD133+were not different in $\Delta$ LVEF (p=0.355). CD133+ differed in reduction of scar size (p=0.022) and non-viable tissue (p=0.022) as compared to placebo.

Posthoc analysis: Primary endpoint responder (R: $\Delta$LVEF≥5%) group showed major gain in $\Delta$LVEF (17.6% 6 m/0; placebo vs. CD133+:+13.9 vs.+19.1%; p=0.066). Non-responders (NR) (LVEF<5% 6 mo/0) (36% in CD133+ and 43.5% in placebo) were preoperatively characterized in peripheral blood by elevated SH2B3 mRNA expression (p=0.032-one-sided/p=0.073two-sided NRvsR), reduced thrombocytes (p=0.004 NRvsR) and EPC (NRvsR CD133+ 117+ p=0.027) in the presence of increased EPO (p=0.02 NRvsR). Longterm survival was reduced in NR (Kaplan-Meier RvsNR HR 0.3, p=0.067). Using machine learning 10 preoperative parameters were identified allowing discrimination of responder or non-responder patients.

SH2B3 expression was analysed in peripheral blood of responders and non-responders. Whole blood samples were obtained from 21 patients before coronary artery bypass graft (CABG) revascularization. Relative expression of SH2B3 (a) and corresponding $\Delta$CT values (b) were calculated using the $2^{-\Delta\Delta CT}$ method. All values are presented as mean±SEM and normalized to GAPDH and POLR2A. n=13 (responder); n=8 (non-responder). $\Delta$CT values: p=0.033 (two-tailed t-test). The obtained data are depicted in FIG. 1. The results demonstrate that SH2B3 expression is significantly higher in non-responders versus responders.

The clinical trial described above demonstrates evidence of pivotal regulation of cardiac regeneration associated with peripheral blood EPC, thrombocyte, and SH2B3 levels. This allows diagnostic selection of highly responsive patients and gives access to tailor-made regenerative therapies for patients.

Example 2

Determination of SH2B3 gene expression was conducted by sampling of whole blood, followed by RT-PCR.

TABLE 1

Determination of SH2B3 gene expression applying RT-PCR.

| Target: SH2B3 | Sampling of whole blood (EDTA) | Method: RT-PCR | Measurement of RNA Integrity Number (RIN) using the Agilent 2100 Bioanalyzer. Samples with RIN ≥7 were used for further experiments. Measurement of RNA concentration and purity using the NanoDrop 1000. The two endogenous normalization controls POLR2A TaqMan ® Gene Expression Assay (Hs00172187_m1, Thermo Fisher Scientific) and GAPDH (4326317E, Thermo Fisher Scientific) were used for ΔΔCT method. |
|---|---|---|---|

Example 3

Native samples of peripheral blood (EDTA blood) were used for quantitative Real Time-PCR using LightCycler 480 II (Roche Deutschland Holding GmbH).

Isolation of RNA from 1 ml whole blood aliquots (stored at −80° C.) was performed using the GeneJET Stabilized and Fresh Whole Blood RNA Kit (Thermo Fisher Scientific). Reverse transcription was performed using the High-Capacity cDNA Reverse Transcription Kit (Thermo Fisher Scientific). RT-PCR was performed using the StepOnePlus RT PCR System (Applied Biosystems™). cDNA (30 ng for each reaction), TaqMan® Universal PCR Master Mix (Thermo Fisher Scientific) and SH2B3 TaqMan® Gene Expression Assay (Hs01081959_g1, Thermo Fisher Scientific) were used. Three technical replicates were performed. To calculate the relative expression ratio of SH2B3 the ΔΔCT method was applied.

Example 4

Native human tissue samples were used instead of whole blood samples. The determination of SH2B3 was conducted by RT-PCR as described in any of Examples 2 or 3.

Example 5

Cultured human or non-human cells and tissue was used instead of whole blood samples. The determination of SH2B3 was conducted by RT-PCR as described in any of Examples 2 or 3.

Example 6

Genetically modified human or non-human cells, tissues and organs were used instead of whole blood samples. The determination of SH2B3 was conducted by RT-PCR as described in any of Examples 2 or 3.

Abbreviations:
  CD=Cluster of Differentiation
  CABG=Coronary artery bypass grafting
  BM=Bone marrow
  QC=Quality control performed within CD133+ isolated from BM
  LVEF=Left ventricular ejection fraction
  MNC=Mononuclear cells
  PB=Peripheral blood
  IHG=Analysis performed in accordance with ISHAGE guidelines
  EPC=Endothelial progenitor cells, EPC panel, CDs measured in PB
  CEC=Circulating endothelial cells, CEC panel, CDs measured in PB
  SCF=Stem Cell Factor
  VEGF=Vascular Endothelial Growth Factor
  VEGFR2/KDR/VEGF-REC=Vascular Endothelial Growth Factor Receptor 2/Kinase Insert Domain Receptor

Example 7

The influence of induced SH2B3 expression in peripheral blood on tissue regeneration is depicted in Table 2 below.

TABLE 2

|  | SH2B3 normal | increased |
|---|---|---|
| peripheral ischemia and inflammation (HIF, TNF) | ↑ | ↑ |
| Endothelial activation VEGF Rec Expression | ↑ | ↑ |
| EPO, VEGF release peripheral blood | ↑ | ↑ |
| bone marrow stem cell proliferation/release EPC CD133⁺ | ↑ | ↓ |
| angiogenesis stimulation by EPC binding to peripheral VEGF-REC | ↑ | ↓ |
| peripheral tissue repair and sufficient oxygenation | ↑ | ↓ |

The principal characteristics of reduced bone marrow stimulation and angiogenesis response in non-responders vs. responders at baseline is shown in Table 3 below.

TABLE 3

| SH2B3 | ↑ |
|---|---|
| Thrombocytes | ↓ |
| CD133⁺ EPC | ↓ |
| CEC | ↑ |
| VEGF | ↑ |
| EPO | ↑ |
| Hill-CFU | ↓ |

The invention claimed is:

1. A method for treating a human subject in need of autologous intramyocardial CD133+purified bone marrow stem cell transplantation wherein the human subject's SH2B3 gene expression is lower than that of a non-responder, the method comprising:
   i. sampling a tissue from the human subject to determine the human subject's tissue SH2B3 gene expression and sampling a tissue from a plurality of non-responders to determine the non-responder's SH2B3 gene expression, to determine that the SH2B3 gene expression in the subject's tissue is lower than the SH2B3 gene expression in the non-responder's tissue,
   ii. treating the subject with autologous intramyocardial CD133+purified bone marrow stem cell transplantation.

2. The method of claim 1, wherein the tissue is peripheral blood.

3. The method according to claim 1, where the subject suffers from coronary artery disease, and atherosclerosis.

4. The method according to claim 1, wherein the SH2B3 gene expression in the subject's tissue is determined by analysis of covariance (ANCOVA) and/or two-sample t test of the tissue from a plurality of non-responders.

5. The method according to claim 1, wherein determining SH2B3 gene expression is by RT-PCR or qPCR.

6. The method according to claim 1, wherein determining SH2B3 gene expression is by quantitative detection of SH2B3 mRNA by RT-PCR or qPCR.

7. The method according to claim 1, wherein determining SH2B3 gene expression comprises determining SH2B3 gene expression normalized to GAPDH expression and POLR2A expression in the same tissue.

* * * * *